United States Patent
Petri

Patent Number: 5,166,306
Date of Patent: Nov. 24, 1992

[54] FLAME-RESISTANT POLYCARBONATE CONTAINING UNITS FROM HALOGENATED PYRIMIDINE COMPOUNDS IN THE POLYMER CHAIN

[75] Inventor: Alberto Petri, Milan, Italy

[73] Assignee: Enichem Technoresine S.p.A., Palermo, Italy

[21] Appl. No.: 815,128

[22] Filed: Dec. 27, 1991

Related U.S. Application Data

[63] Continuation of Ser. No. 443,905, Nov. 30, 1989, Pat. No. 5,098,989.

[30] Foreign Application Priority Data

Dec. 2, 1988 [IT] Italy ............................ 22837 A/88

[51] Int. Cl.$^5$ .............................................. C08G 64/12
[52] U.S. Cl. .................... 528/176; 528/174; 528/175; 528/190; 528/194; 528/196; 528/201; 528/202; 528/371
[58] Field of Search ............... 528/176, 174, 175, 190, 528/194, 196, 201, 202, 371

[56] References Cited

U.S. PATENT DOCUMENTS

| | | | |
|---|---|---|---|
| 4,786,707 | 11/1988 | Manaresi et al. | 528/175 |
| 4,788,273 | 11/1988 | Petri | 528/176 |
| 4,789,723 | 12/1988 | Manaresi et al. | 528/175 |
| 4,795,797 | 1/1989 | Petri | 528/176 |
| 4,798,882 | 1/1989 | Petri | 528/190 |

*Primary Examiner*—Harold D. Anderson
*Attorney, Agent, or Firm*—Hedman, Gibson & Costigan

[57] ABSTRACT

Flame-resistant thermoplastic branched polycarbonates of high molecular weight are prepared from:
(1) a carbonate precursor;
(2) at least one dihydroxyaromatic compound of formula:

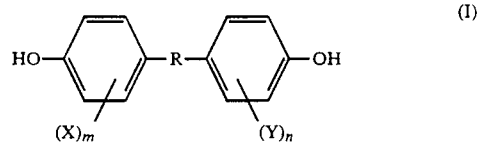

where:
R is a single bond, or a substituted or non-substituted linear or branched $C_1$–$C_5$ alkylene radical, or a group chosen from O, S, $SO_2$ and CO;
X and Y, which may be the same or different, are H or $CH_3$;
m and n, which may be the same or different, are whole numbers from 1 to 4;
(3) at least one halogenated pyrimidine compound of formula:

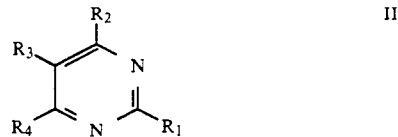

where: $R_2$, $R_3$, $R_4$, which may be the same or different, are chlorine or bromine or hydrogen, on condition that at least one is chlorine or bromine;
$R_1$ is chlorine or bromine, or a radical of formula:

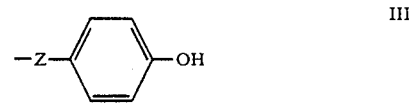

where Z is NH or S or O;
(4) at least one polyfunctional organic compound as branching agent, characterized by possessing at least three equal or different groups chosen from the groups OH, COOH, COCl and $SO_2Cl$.

19 Claims, No Drawings

FLAME-RESISTANT POLYCARBONATE CONTAINING UNITS FROM HALOGENATED PYRIMIDINE COMPOUNDS IN THE POLYMER CHAIN

This is a continuation, of application Ser. No. 07/443,905, filed Nov. 30, 1989, now U.S. Pat. No. 5,098,989.

This invention relates to thermoplastic branched polycarbonates of high molecular weight possessing flame-resistant properties (self-extinguishing).

Polycarbonates are known in the art for their excellent physical and mechanical properties such as their high impact strength and their considerable dimensional and thermal stability. Because of the constantly increasing requirement for materials which for safety reasons possess not only excellent mechanical properties but also flame-resistant properties, various methods have been devised in the art for making polycarbonates self-extinguishing.

One of the most commonly used methods is based on introducing halogens, mainly bromine and chlorine, into the polycarbonate. The halogens can be introduced into the polymer in the form of additives by using generally polyhalogenated organic substances as described for example in U.S. Pat. No. 3,357,942, if desired together with other additives of synergic action such as antimony oxide (J. T. Howarth et al., Plastic World, p. 64-74, March 1973). It is also known to chemically bond the halogens to the polymer chain by using bifunctional phenols such as tetrabromobisphenol A and tetrachlorobisphenol A as co-monomers in the preparation of the polycarbonate (U.S. Pat. No. 3,334,154).

Halogenated substances of the known art, whether additives or monomers to incorporate in the polymer chain, must however be used in rather large quantities to give the polycarbonate the required self-extinguishing properties. Although the presence of large halogen quantities in the polycarbonate on the one hand makes the polymer able to resist the flame, on the other hand it leads to degradation of the polycarbonate during its working, to thus cause deterioration in the physical and mechanical properties of the non-halogenated polycarbonate.

Moreover, the high temperatures necessary for working the polycarbonate can cause degradation of the halogenated compounds, with release of hydrohalogen acids and consequent damage to the machines by corrosion.

Thus the technical problem still unsolved is to produce polycarbonates possessing flame-resistant properties which preserve all their inherent chemical, physical and mechanical properties intact.

It has now been found possible to solve said problem by preparing thermoplastic branched polycarbonates of high molecular weight possessing flame-resistant properties, by using a branching agent and a halogenated pyrimidine compound as co-monomer in the preparation of the polycarbonate, said compound being used in small quantities which are in any event less than such as would lead to undesirable changes in the polymer properties.

More particularly, according to the present invention, said thermoplastic branched polycarbonates of high molecular weight possessing flame-resistant properties are prepared from:
(1) a carbonate precursor;
(2) at least one dihydroxyaromatic compound of formula:

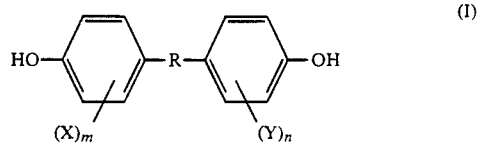

where:
R is a single bond, or a substituted or non-substituted linear or branched $C_1$-$C_5$ alkylene radical, or a group chosen from O, S, $SO_2$ and CO;
X and Y, which may be the same or different, are H or $CH_3$;
m and n, which may be the same or different, are whole numbers from 1 to 4;
(3) at last one halogenated pyrimidine compound of formula:

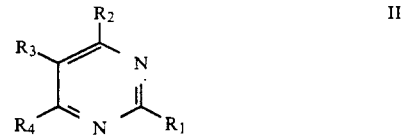

where: $R_2$, $R_3$, $R_4$, which may be the same or different, are chlorine or bromine or hydrogen, on condition that at least one is chlorine or bromine;
$R_1$ is chlorine or bromine, or a radical of formula:

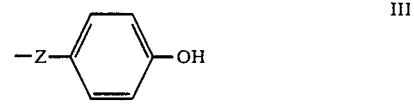

where Z is NH or S or O;
(4) at least one polyfunctional organic compound as branching agent, characterised by possessing at least three equal or different groups chosen from the groups OH, COOH, COCl and $SO_2Cl$. For said polycarbonates to exhibit flame-resistant properties it is sufficient for the molar ratio of (3) to (2) to be between 0.01/100 and 6/100, and preferably between 0.05/100 and 4/100. The following are some examples of dihydroxyaromatic compounds (2) which can be used:
4,4'-dihydroxydiphenyl
2,2-bis(4-hydroxyphenyl)propane (bisphenol A)
2,2-bis(3,5-dimethyl-4-hydroxyphenyl)propane;
bis(4-hydroxyphenyl)methane.

In addition to said dihydroxyaromatic compounds, compounds with a single bivalent aromatic ring such as resorcin and hydroquinone can also be used.

The halogenated pyrimidine compounds (3) of formula II can be prepared using known methods of organic chemistry, or can be products easily obtained commercially, such as 2,4,6-trichloropyrimidine and 2,4,5,6-tetrachloropyrimidine. The pyrimidine compounds in which $R_1$ is the radical of formula III in which Z is NH are new and can be prepared, for example, by reacting a pyrimidine compound of formula II in which $R_1$ is chlorine with p-aminophenol, conducting the reaction in an organic solvent such as acetone at a temperature of about 50°-60° C. and using a p-aminophenol quantity which is double the stoichiometric, so as to bind the as-evolved hydrogen chloride.

The compounds in which Z is S or O can be prepared in a similar manner by using suitable reagents.

Some examples of halogenated pyrimidine compounds suitable for the purposes of the present invention are:
2,4,6-trichloropyrimidine
2,4,5,6-tetrachloropyrimidine
2,6-dichloropyrimidine
2,4,6-tribromopyrimidine
2,4,5,6-tetrabromopyrimidine
2,6-dibromopyrimidine
6-chloro-2-(p-hydroxy)anilinepyrimidine
4,6-dichloro-2-(p-hydroxy)anilinepyrimidine
4,5,6-trichloro-2-(p-hydroxy)anilinepyrimidine.

The compounds particularly preferred are:
2,4,6-trichloropyrimidine
2,4,5,6-tetrachloropyrimidine
2,6-dichloropyrimidine.

The carbonate precursor can be phosgene or a chloroformylterminated polycarbonate oligomer (MW between 400 and 2000) prepared by reacting phosgene with a dihydroxyaromatic compound of formula I, or it can be a diaryl, dialkyl or alkylaryl ester of carbonic acid, such as diphenyl carbonate.

The organic polyfunctional compounds for use as branching agents are compounds known in the art and are characterised by possessing at least three equal or different functional groups chosen from the groups OH, COOH, COCl and $SO_2Cl$.

For example, the branching agents used can be those compounds described in Italian Patent Application: 23538 A/84, 20927 A/87 and U.S. Pat. Nos. 4,857,628, 4,789,723, 4,786,707, 4,795,797, 4,788,273, 4,798,882 and U.S. patent application Ser. Nos. 203,705, 203,425.

The following polyfunctional organic compounds are particularly preferred for the purposes of the present invention:
2,4,6-tris(4'-hydroxyphenyl)amino-s-triazine;
3,7-dihydroxy-$\beta$-naphthoic acid;
1,3,5-trihydroxybenzene;
4,4'-methylenebis(3-hydroxy-2-carboxynaphthalene);
tris(4-hydroxyphenyl)methane;
2,3,4,5-tetrachlorocarbonyltetrahydrofuran;
1,3,6-trichlorosulphonylnaphthalenic acid To provide the polycarbonate with branching, it is sufficient for the molar ratio of (4) to (2) to be between 0.01/100 and 5/100, and preferably between 0.05/100 and 2/100.

The flame-resistant polycarbonates of the present invention can be prepared by reacting together, in accordance with one of the polymerization methods usually used to produce polycarbonates, (1) a carbonate precursor, (2) a dihydroxyaromatic compound of formula I, (3) a halogenated pyrimidine compound of formula II, and (4) a polyfunctional organic compound as branching agent, the molar ratio of (3) to (2) varying from 0.01/100 to 6/100 and preferably from 0.5/100 to 4/100, and the molar ratio of (4) to (2) varying from 0.01/100 to 5/100, and preferably from 0.05/100 to 2/100. One of the polymerization methods which can conveniently be used for preparing said polycarbonates is interfacial polycondensation. This method consists of effecting the polymerization reaction in a two-phase system consisting of an aqueous alkaline solution, such as an aqueous sodium hydroxide solution, and an organic solvent immiscible with water such as methylene chloride.

The dihydroxyaromatic compound (2) in dissolved in the aqueous phase, whereas the compounds (3) and (4) can be dissolved either in the organic phase or in the aqueous phase depending on their solubility, In particular, the halogenated pyrimidine compounds (3) are soluble in the organic phase when $R_1$ is chlorine or bromine, whereas they are soluble in the aqueous phase when $R_1$ is a group of formula III.

In contrast, the branching agents (4) are for the most part soluble in the aqueous phase.

Phosgene gas is then bubbled through the two-phase system containing the compounds (2), (3) and (4) and the reaction mixture is maintained at a temperature of between 15° and 25° C. for a period of between 20 minutes and 6 hours, in the presence of a phase transfer catalyst such as triethylamine and a molecular weight regulator such as p-tert.butylphenol.

According to a preferred embodiment of the present invention, the polycarbonates can be prepared using as carbonate precursors chloroformyl-terminating polycarbonate oligomers, which can be prepared by interfacial reaction between phosgene and a dihydroxyaromatic compound of formula I, in the presence of a monofunctional phenol as molecular weight regulator such as p-tert.butylphenol. Said chloroformyl-terminating oligomers, the molecular weight of which varies from 400 to 2000, are then dissolved in a water-immiscible organic solvent and reacted, again by the interfacial polycondensation method, with compounds (2), (3) and (4) in the presence of a phase transfer catalyst.

As an alternative to interfacial polycondensation, the polycarbonates of the present invention can be prepared by the known method of polycondensation in solution.

In this case, phosgene is bubbled through a solution of methylene chloride and pyridine containing the dihydroxyaromatic compound (2), the halogenated pyrimidine compound (3), the branching agent (4) and a monofunctional phenol as molecular weight regulator.

It is also possible to prepare said polycarbonates by transesterification in the molten state, by reacting carbonic acid dialkyl, diaryl or alkylaryl esters as carbonate precursors with the dihydroxyaromatic compound (2), the pyrimidine compound (3) and the branching agent (4) at a temperature of between 100° and 300° C. in the presence of transesterification catalysts.

The polycarbonates prepared by any of the aforesaid methods have a prevalent molecular weight of between 20,000 and 30,000; they preserve all the inherent characteristics of thermoplastic materials intact and are suitable for processing either by injection moulding or by extrusion and/or blow-moulding. Said polycarbonates can be classified as V-0 in their fire behaviour, evaluated by the UL94 code (Underwriters' Laboratories Inc., bulletin S4) and conducted on test pieces of 3.2 mm thickness prepared by compression or injection.

According to said code the materials are classified V-0, V-1 or V-2 based on the results obtained in five tests, in accordance with the following criteria:

V-0: No test piece must show a combustion time exceeding 10 seconds after removal of a bunsen flame. The total combustion time for the five test pieces (ten ignitions) must not exceed 50 seconds. No test piece must allow burning particles to drip and ignite surgical cotton placed vertically under the test piece at a distance of 305 mm.

V-1: No test piece must show a combustion time exceeding 30 seconds after removal of a bunsen flame. The total combustion time for the five test pieces (ten ignitions) must not exceed 250 seconds. No test piece must allow burning particles to drip and ignite surgical cotton placed vertically under the test piece at a distance of 305 mm.

V-2: No test piece must show a combustion time exceeding 30 seconds after removal of a bunsen flame. The total combustion time for the five test pieces (ten ignitions) must not exceed 250 seconds. The test pieces may allow burning particles to drip and ignite surgical cotton placed vertically under the test piece at a distance of 305 mm.

In addition all five test pieces must pass the test prescribed by UL-94 otherwise they are classified on the basis of the behaviour of the worst test piece. For example, if one test piece shows V-2 behaviour whereas the other four show V-0 behaviour, all five test pieces are classified V-2. Finally, if a test piece continues to burn for more than 30 seconds after removing the bunsen flame, it cannot be classified under UL-94 but instead is indicated as a flammable test piece.

The test pieces are also subjected to a fire-behaviour test in accordance with ASTM D 2863-77 which correlates the flammability of a polymer material with the oxygen concentration of the atmosphere in which the test piece is located. This correlation is expressed by the LOI (limiting oxygen index), i.e. the minimum oxygen percentage able to maintain combustion of the test piece in the oxygen-nitrogen atmosphere which flows about the test piece from the bottom upwards.

The following characteristics were also determined on the polycarbonates of the present invention:

Intrinsic viscosity ($n$)

This property is determined in methylene chloride at 20° C. by an Ubbelhode viscometer and is expressed in dl/g.

Melt flow index (MFI)

The melt flow index is evaluated in a melt indexer on an extruded granulate, under a load of 1.2 kg at a temperature of 300° C., in accordance with ASTM D1238.

Impact strength (IZOD)

This is evaluated on notched test pieces at 0° C. in accordance with ASTM D256.

Shear sensitivity (SS)

This quantity is evaluated in a melt indexer on an extruded granulate, under loads of 1.2 and 12 kg at a temperature of 300° C., in accordance with ASTM D1238.

The following experimental examples are given for illustrative purposes only and are not to be taken as limitative of the scope of the invention.

EXAMPLE 1

Preparation of 4,6-dichloro-2-(p-hydroxy) anilinepyrimidine (in formula II: $R_3$ is hydrogen; $R_2$ and $R_4$ are Cl; $R_1$ is the radical of formula III in which Z is NH).

25.1 g (230 mmoles) of p-aminophenol dissolved in 120 ml of acetone are placed in a 250 ml 4-neck flask fitted with a magnetic stirrer, thermometer and reflux condenser, operating under an inert gas atmosphere.

21.1 g (115 mmoles) of 2,4,6-trichloropyrimidine dissolved in 30 ml of acetone are then dripped slowly in, and the resultant mixture is kept for 1 hour at reflux temperature (58° C.). On termination of this period, the reaction mixture is poured into 4 liters of demineralized water and the solid product which precipitates is separated by filtration, washed with water and dried.

In this manner 27 g of 4,6-dichloro-2(p-hydroxy) anilinepyrimidine are obtained with a yield of 91.7%.

The product had the following characteristics:

| Melting point (DSC) | 218° C. | | | |
|---|---|---|---|---|
| Equivalent weight (acidimetric) | 253 (theoretical = 256) | | | |
| | Elementary analysis: | | | |
| | C | H | N | Cl |
| Experimental % | 47.2 | 2.8 | 16.3 | 27.7 |
| Theoretical % | 46.9 | 2.8 | 16.4 | 27.7 |

The product structure was confirmed by NMR spectroscopic analysis.

EXAMPLE 2

Preparation of 4,5,6-trichloro-2-(p-hydroxy) anilinepyrimidine (in formula II; $R_2$, $R_3$ and $R_4$ are Cl; $R_1$ is the radical of formula III in which Z is NH).

The procedure of Example 1 is followed, but using 27 g (247 mmoles) of p-aminophenol and 26.9 g (124 mmoles) of 2,4,5,6-tetrachloropyrimidine.

34.1 g of 4,5,6-trichloro-2-(p-hydroxy) anilinepyrimidine are obtained with a yield of 95%.

The product had the following characteristics:

| Melting point (DSC) | 208° C. | | | |
|---|---|---|---|---|
| Equivalent weight (acidimetric) | 287 (theoretical = 290.5) | | | |
| | Elementary analysis: | | | |
| | C | H | N | Cl |
| Experimental % | 41.3 | 2.1 | 14.3 | 36.6 |
| Theoretical % | 41.3 | 2.1 | 14.5 | 36.6 |

The product structure was confirmed by NMR spectroscopic analysis.

EXAMPLE 3

84 g of bisphenol A, 534 mg of 2,4,6-tris(4-hydroxyphenyl) aminos-triazine (equal to 0.36 mol % on the bisphenol A), 65.2 g of sodium hydroxide dissolved in 650 ml of water, 20 mg of sodium dithionate (as reducing agent to prevent the formation of coloured by-products) and 6.3 ml of a 0.5N aqueous triethylamine solution are fed under a nitrogen stream into a 3 liter glass reactor temperature-controlled at 25° C.

2.4 g of p-tert.butylphenol and 608 mg of 2,4,6-trichloropyrimidine (equal to 0.9 mol % on the bisphenol A) dissolved in 1300 ml of methylene chloride are then added and 44 g of phosgene gas are bubbled over a time of 30 minutes through the mixture, which is subjected to vigorous stirring.

The reaction proceeds for 2 hours, aqueous sodium hydroxide (20 wt %) being added to keep the pH continuously greater than 11. The mixture is then diluted with 500 ml of methylene chloride and the organic phase is separated and washed successively with 300 ml of water (twice), 800 ml of aqueous 0.15N sodium hydroxide (3 times), 600 ml of water (twice), 800 ml of 0.1N hydrochloric acid and finally with 600 ml portions of water until neutral.

The polymer is recovered by distilling the organic solvent and is dried and ground to obtain a powder.

The polycarbonate obtained in this manner is then extruded at 260° C. and the extrusion cooled and granulated. The granules are moulded either by compression (280° C., 50 kg/cm$^2$) or by injection (300° C.) to obtain test pieces of size 127×6.5×3.2 mm.

Five test pieces are subjected to the fire behaviour test described in UL 94. They are found to be V-0, in accordance with the data given in Table 1.

The other polymer characteristics are given in Table 2.

EXAMPLE 4

84 g of bisphenol A, 2.1 g of 4,6-dichloro-2-(p-hydroxy) anilinepyrimidine (equal to 2.2 mol % on the bisphenol A), 534 mg of 2,4,6-tris(4-hydroxyphenyl) amino-s-triazine (equal to 0.36 mol % on the bisphenol A), 65.2 g of sodium hydroxide dissolved in 650 ml of water, 20 mg of sodium dithionate (as reducing agent to prevent the formation of coloured by-products) and 6.3 ml of a 0.5N aqueous triethylamine solution are fed under a nitrogen stream into a 3 liter glass reactor temperature-controlled at 25° C.

1.7 g of p-tert.butylphenol dissolved in 1300 ml of methylene chloride are then added and 44 g of phosgene gas are bubbled over a time of 30 minutes through the mixture, which is subjected to vigorous stirring.

The reaction proceeds for 2 hours, aqueous sodium hydroxide (20 wt %) being added to keep the pH continuously greater than 11. The mixture is then diluted with 500 ml of methylene chloride and the organic phase is separated and washed successively with 300 ml of water (twice), 800 ml of aqueous 0.15N sodium hydroxide (3 times), 600 ml of water (twice), 800 ml of 0.1N hydrochloric acid and finally with 600 ml portions of water until neutral.

The polymer is recovered by distilling the organic solvent, and is dried and ground to obtain a powder.

The polycarbonate obtained in this manner is then extruded at 260° C. and the extrusion cooled and granulated. The granules are moulded either by compression (280° C., 50 kg/cm$^2$) or by injection (300° C.) to obtain test pieces of size 127×6.5×3.2 mm.

Five test pieces are subjected to the fire behaviour test described in UL 94. They are found to be V-0, in accordance with the data given in Table 1.

The other polymer characteristics are given in Table 2.

EXAMPLE 5

Example 4 is repeated using the same operating method and reactant quantities, with the exception that no halogenated pyrimidine compound is used.

The polycarbonate obtained is found to be V-2 in accordance with UL 94 (see Table 1).

The other polymer characteristics are given in Table 2.

EXAMPLE 6

253.8 g of polycarbonate chloroformyl-terminating oligomers (average molecular weight 681, chloroformyl terminal groups=2758 meq/kg, hydroxyl terminal groups=180 meq/kg) prepared from bisphenol A, phosgene and p-tert.butylphenol are dissolved in 850 ml of methylene chloride and fed under nitrogen into a glass reactor of 2.5 liters capacity temperature controlled at 25° C.

To the solution, mechanically stirred by a double-anchor device (300 RPM) are then added, in the stated order, 50 ml of methylene chloride containing 1.03 g of 2,4,6-trichloropyrimidine (equal to 0.48 mol % on the bisphenol A), 50 ml of water containing 1.71 g of 2,4,6-tris(4'-hydroxyphenyl) amino-s-triazine) equal to 0.36 mol % on the bisphenol A), 1.0 g of caustic soda, 31 mg of sodium dithionate and 7 ml of an aqueous 0.05N triethylamine solution. After 40 minutes 350 ml of water are added containing 65.9 g of bisphenol A, 24.45 g of caustic soda and 31 mg of sodium dithionate.

115 ml of a 20 wt % aqueous caustic soda solution are then added over a period of 10 minutes using a metering pump. After 3 hours the reaction mixture is poured into 2200 ml of methylene chloride; the organic phase is then separated and washed, in the stated order, with 900 ml of water (twice), 1300 ml of 0.15N aqueous sodium hydroxide (3 times), 900 ml of water (twice) and 1300 ml of 0.1N hydrochloric acid, and finally with 900 ml portions of water until neutral.

The polymer is recovered by distilling the organic solvent, and is dried and ground to obtain a powder.

The polycarbonate obtained in this manner is then extruded at 260° C. and the extrusion cooled and granulated.

The granules are moulded by injection or compression to obtain test pieces of size 127×6.5×3.2 mm.

Five test pieces are subjected to the fire behaviour test described in UL 94 and are found to be V-0, in accordance with the data given in Table 1.

The other polycarbonate characteristics are given in Table 2.

EXAMPLE 7

Example 6 is repeated using the same operating method and reactant quantities, except that 2.05 g of bis 2,4,6-trichloropyrimidine (0.95 mol % on the bisphenol A) are added.

The polycarbonate obtained is found to be V-0 at the fire behaviour test, evaluated in accordance with UL 94 (see Table 1). The other polymer characteristics are given in Table 2.

EXAMPLE 8

Example 6 is repeated using the same operating method and reactant quantities, except that 1.22 g of 2,4,5,6-tetrachloropyrimidine (0.48 mol % on the bisphenol A) are added instead of the 2,4,6-trichloropyrimidine.

The polycarbonate obtained is found to be V-0 at the fire behaviour test, evaluated in accordance with UL 94 (see Table 1). The other polymer characteristics are given in Table 2.

EXAMPLE 9

Example 8 is repeated using the same operating method and reactant quantities, except that 2.44 g of 2,4,5,6-tetrachloropyrimidine (0.95 mol % on the bisphenol A) are added.

The polycarbonate obtained is found to be V-0 at the fire behaviour test, evaluated in accordance with UL 94 (see Table 1). The other polymer characteristics are given in Table 2.

EXAMPLE 10

253.8 g of polycarbonate chloroformyl-terminating oligomers (average molecular weight 681, chloroformyl terminal group=2758 meq/kg, hydroxyl terminal groups=180 meq/kg) prepared from bisphenol A, phosgene and p-tert.butylphenol are dissolved in 900 ml of methylene chloride and fed under nitrogen into a glass reactor of 2.5 liters capacity temperature controlled at 25° C. To the solution, mechanically stirred by a double-anchor device (300 RPM) are then added, in the stated order, 50 ml of water containing 8.96 g of 4,6-dichloro-2-(p-hydroxy) anilinepyrimidine (equal to 3 mol % on the bisphenol A), 1.71 g of 2,4,6-tris(4'-hydroxyphenyl) amino-s-triazine (equal to 0.36 mol % on the bisphenol A), 2.0 g of caustic soda, 31 mg of sodium dithionate and 7 ml of an aqueous 0.05N triethylamine solution.

After 40 minutes 350 ml of water are added containing 65.9 g of bisphenol A, 24 g of caustic soda and 31 mg of sodium dithionate. 115 ml of a 20 wt % aqueous caustic soda solution are then added over a period of 10 minutes using a metering pump.

After 3 hours the mixture is poured into 2200 ml of methylene chloride; the organic phase is then separated and washed, in the stated order, with 900 ml of water (twice), 1300 ml of 0.15N aqueous sodium hydroxide (3 times), 900 ml of water (twice) and 1300 ml of 0.1N hydrochloric acid, and finally with 900 ml portions of water until neutral.

The polymer is recovered by distilling the organic solvent, and is dried and ground to obtain a powder.

The polycarbonate obtained in this manner is then extruded at 260° C. and the extrusion cooled and granulated.

The granules are moulded by injection or compression to obtain test pieces of size 127×6.5×3.2 mm.

Five test pieces are subjected to the fire behaviour test described in UL 94 and are found to be V-0, in accordance with the data given in Table 1.

The other polycarbonate characteristics are given in Table 2.

EXAMPLE 11

Example 10 is repeated using the same operating method and reactant quantities, except that no halogenated pyrimidine compound is added.

The polycarbonate obtained is found to be V-2 at the fire behaviour test, evaluated in accordance with UL 94 (see Table 1). The other polymer characteristics are given in Table 2.

TABLE 1

| Ex. | Total combustion time of 5 test pieces (10 ignitions (seconds) | Maximum combustion time per test piece (2 ignitions) (seconds) | Classification UL-94 |
|---|---|---|---|
| 3 | 39 | 8 | V-0 |
| 4 | 48 | 10 | V-0 |
| 5 | 99 | 22 | V-2 |
| 6 | 31 | 8 | V-0 |
| 7 | 37 | 10 | V-0 |
| 8 | 46 | 10 | V-0 |
| 9 | 37 | 9 | V-0 |
| 10 | 34 | 9 | V-0 |
| 11 | 110 | 24 | V-2 |

TABLE 2

| Ex. | [η] 20° C. CH$_2$Cl$_2$ (dl/g) | LOI % | Impact (IZOD) (J/m) | MFI (300° C.; 1.2 kg) | SS (300° C.; 1.2 & 12 kg) |
|---|---|---|---|---|---|
| 3 | 0.554 | 34 | 740 | 5.2 | 23.9 |
| 4 | 0.586 | 32 | 721 | 3.9 | 23.8 |
| 5 | 0.520 | 27 | 772 | 7.6 | 13.6 |
| 6 | 0.623 | 33 | 794 | 2.0 | 29.3 |
| 7 | 0.525 | 32 | 702 | 6.8 | 19.6 |

TABLE 2-continued

| Ex. | [η] 20° C. CH$_2$Cl$_2$ (dl/g) | LOI % | Impact (IZOD) (J/m) | MFI (300° C.; 1.2 kg) | SS (300° C.; 1.2 & 12 kg) |
|---|---|---|---|---|---|
| 8 | 0.642 | 32 | 800 | 1.7 | 28.3 |
| 9 | 0.564 | 35 | 744 | 4.8 | 25.4 |
| 10 | 0.575 | 34 | 723 | 4.2 | 23.4 |
| 11 | 0.544 | 28 | 802 | 6.0 | 13.5 |

I claim:

1. A thermoplastic branched polycarbonate of high molecular weight possessing flame-resistant properties, deriving from:
   (1) a carbonate precursor;
   (2) at least one dihydroxyaromatic compound of formula

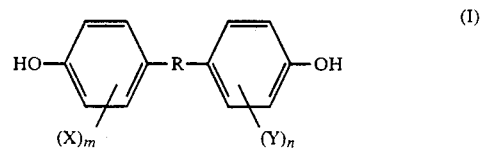

where:
R is a single bond, or R represents a substituted or non-substituted linear or branched C$_1$-C$_5$ alkylene radical, or R is selected from the group consisting of O, S, SO$_2$ and CO;
X and Y, which are the same or different, are H or CH$_3$;
m and n, which are the same or different, are whole numbers from 1 to 4;
   (3) at least one halogenated pyrimidine compound of formula:

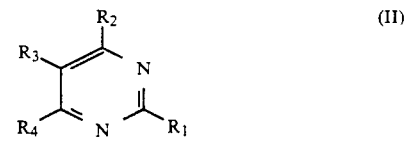

where: R$_2$, R$_3$, R$_4$, which are the same or different, are chlorine or bromine or hydrogen, on condition that at least one is chlorine or bromine;
R$_1$ is chlorine or bromine;
   (4) at least one polyfunctional organic compound as branching, having at least three equal of different groups selected from the group consisting of OH, COOH, COCl and SO$_2$Cl.

2. A polycarbonate as defined in claim 1, having a molar ratio of (3) to (2) between 0.01/100 and 6/100.

3. A polycarbonate as defined in claim 2, having a molar ratio of (3) to (2) between 0.05/100 and 5/100.

4. A polycarbonate as defined in claim 1, having a molar ratio of (4) to (2) between 0.01/100 and 5/100.

5. A polycarbonate as defined in claim 4, having a molar ratio of (4) to (2) between 0.05/100 and 2/100.

6. A polycarbonate as defined in claim 1, wherein said carbonate precursor (1) is selected from the group consisting of phosgene, chloroformyl-terminating polycarbonate oligomers having a molecular weight of between 400 and 2000, and carbonic acid diaryl, dialkyl and arylalkyl esters.

7. A polycarbonate as defined in claim 1, wherein said dihydroxyaromatic compound (2) is selected from the group consisting of:
4,4'-dihydroxydiphenyl;

2,2-bis(4-hydroxyphenyl)propane;
2,2-bis(3,5-dimethyl-4-hydroxyphenyl)propane; and
bis(4-hydroxyphenyl)methane.

8. A polycarbonate as defined in claim 1, wherein said pyrimidine compound (3) is selected from the group consisting of:
2,4,6-trichloropyrimidine;
2,4,5,6-tetrachloropyrimidine;
2,6-dichloropyrimidine;
2,4,6-tribromopyrimidine;
2,4,5,6-tetrabromopyrimidine; and
2,6-dibromopyrimidine.

9. A polycarbonate as defined in claim 8 wherein said pyrimidine compound (3) is selected from the group consisting of:
2,4,6-trichloropyrimidine;
2,4,5,6-tetrachloropyrimidine; and
2,6-dichloropyrimidine.

10. A polycarbonate as defined in claim 1, wherein said polyfunctional compound is selected from the group consisting of:
2,4,6-tris(4'-hydroxyphenyl)amino-s-triazine;
3,7-dihydroxy-β-naphthoic acid;
1,3,5-trihydroxybenzene;
4,4'-methylenebis(3-hydroxy-2-carboxynaphthalene);
tris(4-hydroxyphenyl)methane;
2,3,4,5-tetrachlorocarbonyltetrahydrofuran; and
1,3,6-trichlorosulphonylnapthalenic acid.

11. A method for preparing a polycarbonate as defined in claim 1, comprising reacting together (1) a carbonate precursor, (2) a dihydroxyaromatic compound of formula (I), (3) a halogenated pyrimidine compound of formula (II) and (4) a polyfunctional organic compound as branching agent, the molar ratio of (3) to (2) varying from 0.01/100 to 6/100 and the molar ratio of (4) to (2) varying from 0.01/100 to 5/100.

12. A method as defined in claim 11, wherein said carbonate precursor is selected from the group consisting of phosgene, chloroformyl-terminating polycarbonate oligomers having a molecular weight of between 400 and 2000, and carbonic acid diaryl, dialkyl and arylalkyl esters.

13. A method as defined in claims 12, wherein said carbonate precursor comprises chloroformyl-terminating polycarbonate oligomers having a molecular weight of between 400 and 2000.

14. A thermoplastic branched polycarbonate of high molecular weight possessing flame resistant properties produced from:
(1) a carbonate precursor;
(2) at least one dihydroxyaromatic compound of the formula:

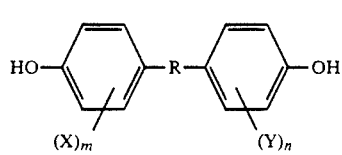

where:
R is a single bond or R represents a substituted or non-substituted linear or branched $C_1$–$C_5$ alkylene radical, or R is selected from the group consisting of O, S, $SO_2$, and CO;
X and Y, which are the same or different, are H or $CH_3$; and
m and n, which are the same or different, are whole numbers from 1 to 4;
(3) at least one halogenated pyrimidine compound of the formula:

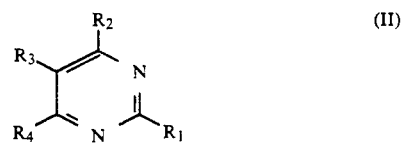

where $R_2$, $R_3$ and $R_4$, which are the same or different, are chlorine, bromine or hydrogen, on condition that at least one is chlorine or bromine; and $R_1$ is a radical of the formula

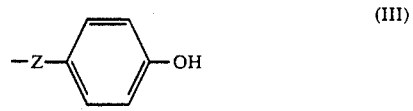

where Z is NH, S or O; and
(4) a polyfunctional organic compound as a branching agent having at least three equal or different functional groups selected from the group consisting of COOH, COCl and $SO_2Cl$.

15. A thermoplastic branched polycarbonate as defined in Claim 14 wherein Z is S.

16. A thermoplastic branched polycarbonate as defined in Claim 14 wherein Z is O.

17. A method for preparing a polycarbonate as defined in Claim 14 comprising reacting together (1) a carbonate precursor, (2) a dihydroxyaromatic compound of formula (I), (3) a halogenated pyrimidine compound of formula (II) and (4) a polyfunctional organic compound as branching agent, the molar ratio of (3) to (2) varying from 0.01/100 to 6/100 and the molar ratio of (4) to (2) varying from 0.01/100 to 5/100.

18. A method as defined in Claim 17 wherein said carbonate precursor is selected from the group consisting of phosgene, chloroformyl-terminating polycarbonate oligomers having a molecular weight of between 400 and 2000, and carbonic acid diaryl, dialkyl and arylalkyl esters.

19. A method as defined in Claim 18, wherein said carbonate precursor comprises chloroformyl-terminating polycarbonate oligomers having a molecular weight of between 400 and 2000.

* * * * *

UNITED STATES PATENT AND TRADEMARK OFFICE
CERTIFICATE OF CORRECTION

PATENT NO. : 5,166,306
DATED : November 24, 1992
INVENTOR(S) : Alberto Petri

It is certified that error appears in the above-identified patent and that said Letters Patent is hereby corrected as shown below:

On column 10, line 48 (Claim 1), please insert after "branching" and before " , having" , the word --agent--.

Signed and Sealed this

Sixteenth Day of November, 1993

Attest:

BRUCE LEHMAN

*Attesting Officer*    *Commissioner of Patents and Trademarks*